United States Patent [19]
Matsumura et al.

[11] 4,207,324
[45] Jun. 10, 1980

[54] 1,2-DI-SUBSTITUTED-4-HALOIMIDAZOLE-5-ACETIC ACID DERIVATIVES AND THEIR USE

[75] Inventors: Koichi Matsumura; Naoto Hashimoto; Yoshiyasu Furukawa, all of Osaka, Japan

[73] Assignee: Takeda Chemical Industries, Ltd., Osaka, Japan

[21] Appl. No.: 36,645

[22] Filed: May 7, 1979

[30] Foreign Application Priority Data

May 15, 1978 [JP] Japan .................. 53-57912

[51] Int. Cl.$^2$ .................. A61K 31/415; C07D 233/68
[52] U.S. Cl. .................. 424/273 R; 548/336; 548/337
[58] Field of Search .................. 548/336, 337; 424/273 R

[56] References Cited
U.S. PATENT DOCUMENTS

| | | | |
|---|---|---|---|
| 3,354,173 | 11/1967 | Godefroi et al. | 548/336 |
| 3,772,315 | 11/1973 | Regel et al. | 548/337 |
| 3,932,445 | 1/1976 | Rasmussen | 548/336 |
| 3,991,072 | 11/1976 | Roevens et al. | 548/343 |
| 4,038,286 | 7/1977 | Roevens et al. | 548/343 |
| 4,042,702 | 8/1977 | Rainer | 424/273 P |

Primary Examiner—Natalie Trousof
Attorney, Agent, or Firm—Stevens, Davis, Miller & Mosher

[57] ABSTRACT

Novel imidazole derivatives of the formula

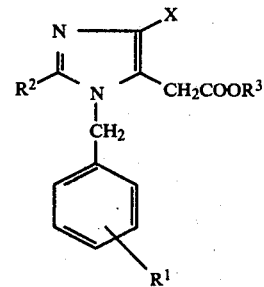

wherein $R^1$ is hydrogen, nitro or amino, $R^2$ is a phenyl, furyl or thieyl group which may be substituted by halogen, lower alkyl, lower alkoxy or di-lower-alkylamino, $R^3$ is hydrogen or lower alkyl and X is halogen, and their physiologically acceptable salts, have excellent diuretic and hypotensive actions.

13 Claims, No Drawings

1,2-DI-SUBSTITUTED-4-HALOIMIDAZOLE-5-ACETIC ACID DERIVATIVES AND THEIR USE

The present inventors have succeeded in producing 1,2-di-substituted-4-haloimidazole-5-acetic acid derivatives of the formula

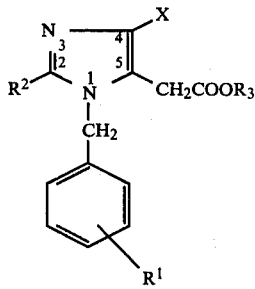

wherein $R^1$ is hydrogen, nitro or amino, $R^2$ is a phenyl, furyl or thienyl group which may be substituted by halogen, lower alkyl, lower alkoxy or di-lower-alkylamino, $R^3$ is hydrogen or lower alkyl and X is halogen, and their salts, which are all new compounds, and further studies on these compounds have unexpectedly revealed that they exhibit excellent diuretic and hypotensive actions and, hence, are of value as diuretic or hypotensive drugs.

Thus, the principal object of this invention is to provide the novel imidazole derivatives (I) and their salts which have the excellent pharmacological actions, and another object is to provide a pharmaceutical composition comprising one or more of these compounds. A further object is to provide an industrially feasible method for producing these compounds. Other objects will be made clear from the description and claims presented hereinafter.

Referring, now, to the formula (I) given above, the nitro or amino group $R^1$ may be present in any desired position on the benzene ring, although it is preferably present in the p-position. The furyl or thienyl group $R^2$ is preferably 2-furyl or 2-thienyl. The phenyl, furyl or thienyl group $R^2$ may be substituted and such nuclear substituent may be halogen, lower alkyl, lower alkoxy or di-lower-alkylamino. The halogen as said substituent is preferably chlorine or bromine; the lower alkyl may be straight-chain or branched and may for example be methyl, ethyl, propyl, isopropyl, isobutyl or tert-butyl, with alkyls of up to 4 carbon atoms being particularly desirable; the lower alkoxy may be straight-chain or branched and may for example be methoxy, ethoxy, propoxy, isopropoxy, butoxy or isobutoxy, with alkoxy groups containing 4 carbon atoms at the maximum being particularly preferred; and the di-lower-alkylamino group may desirably be one containing 4 or fewer carbon atoms, i.e. dimethylamino or diethylamino. These substituents may be present in optional positions of the phenyl, furyl and thienyl rings, and in the case of phenyl, the substitution preferably occurs in the p-position. The lower alkyl group $R^3$ may be straight-chain or branched and may contain up to 4 carbon atoms, e.g. methyl, ethyl, propyl or isobutyl, with methyl and ethyl being preferred. The halogen X may for example be chlorine or bromine.

The above compound (I) can be produced in good yield, for example by solvolyzing a compound of the formula

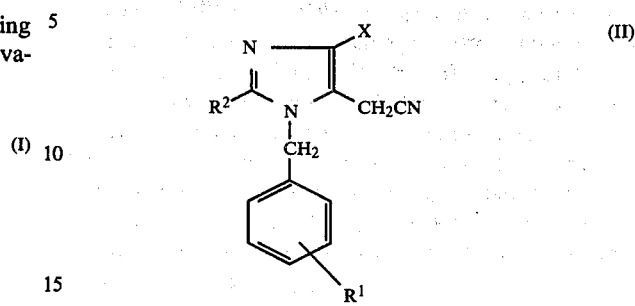

wherein $R^1$, $R^2$ and X have respectively the same meanings as defined hereinbefore.

The solvolysis may be hydrolysis or alcoholysis. The compound (I) wherein $R^3$ is hydrogen is produced when hydrolysis is followed, whereas alcoholysis gives rise to compound (I) where $R^3$ is lower alkyl.

The hydrolysis reaction is generally carried out with an acid or alkali. The acid is preferably a mineral acid such as sulfuric acid or hydrochloric acid. The concentration of sulfuric acid in the reaction system is desirably between about 40% and about 60%, and that of hydrochloric acid is desirably between about 10% and about 20%. When the compound (II) is hardly soluble, about 30 to 50% of acetic acid may be added with advantage. The alkali mentioned above is preferably an alkali metal hydroxide such as sodium hydroxide, potassium hydroxide or lithium hydroxide, and as the solvent, it is advantageous to employ aqueous methanol, aqueous ethanol or the like. This hydrolysis reaction proceeds under heating, and it is normally advantageous to conduct this reaction at an elevated temperature between about 50° C. and about 150° C., preferably near the boiling point of the solvent used, for about 2 to 10 hours. The resulting compound (I) where $R^3$ is hydrogen may be esterified into compound (I) where $R^3$ is lower alkyl. This esterification reaction can be easily carried out, for example by heating a compound (I) where $R^3$ is hydrogen in a solvent containing an alcohol corresponding to the desired alkyl group (the alcohol as such or a mixture of the alcohol with benzene, 1,2-dimethoxyethane or the like) and in the presence of an acid catalyst (e.g. hydrogen chloride, sulfuric acid or methanesulfonic acid) and, if necessary, removing the by-product water from the reaction system.

The alcoholysis reaction is generally carried out by heating a compound (II) in an alcohol corresponding to the lower alkyl group $R^3$ with the addition of an acid. The acid is preferably a mineral acid such as sulfuric acid or hydrochloric acid, the amount of which is desirably about 1 to 10 molar equivalents based on compound (II). Generally, this reaction is preferably conducted at an elevated temperature of about 50° to 100° C. and, for still better results, near the boiling point of the alcohol used, for about 1 to 10 hours. The resulting compound where $R^3$ is lower alkyl can be tranformed upon hydrolysis into compound (I) where $R^3$ is hydrogen. This hydrolysis reaction is effected by means of an alkali or acid, an alkali being preferred. The alkali for this purpose is preferably an alkali metal hydroxide such as sodium hydroxide, potassium hydroxide or lithium hydroxide. Using aqueous methanol, aqueous ethanol or the like as the solvent, this reaction is carried out at about 20° to 100° C. for 5 to 20 hours.

Where $R^1$ in the resulting compound (I) is nitro, it may be reduced to compound (I) where $R^1$ is amino. This reduction may be conducted by a conventional procedure, e.g. in the tin-HCl, iron-HCl or zinc-acetic acid system or by catalytic reduction with the aid of 5–10% palladium-on-carbon, Raney nickel or platinum, to mention but a few preferred catalysts.

The resulting compound (I) can be easily separated from the reaction system by conventional separatory-purification procedures such as extraction, concentration, neutralization, filtration, recrystallization, column chromatography, etc. According to the type of $R^1$, $R^2$ and $R^3$ therein, compound (I) may be obtained as a salt with a base or as an acid addition salt. Thus, compound (I) where $R^3$ is hydrogen can be transformed in the per se known manner into a physiologically acceptable salt with a base, such as an alkali metal salt (e.g. sodium salt, potassium salt, etc.), alkaline earth metal salt (e.g. calcium salt, etc.), for instance. The compound (I) where $R^1$ is amino or/and which has a di-lower-alkylamino group on its ring $R^2$ can be transformed in the per se conventional manner into a physiologically acceptable acid addition salt such as a mineral acid salt (e.g. hydrochloride, sulfate, etc.)

The compounds (I) and their physiologically acceptable salts thus produced exhibit excellent diuretic and hypotensive actions in animals, particularly in mammalians (e.g. man, dog, rabbit, rat, etc.), and these actions plus their low toxicity make these compounds valuable for the treatment of edema and hypertension as may be induced by various causes. For such medicinal purposes, the compound (I) or its salt can be safely administered as it is or as formulated with an appropriate pharmaceutically acceptable carrier, vehicle or diluent in any of such varied dosage forms as powders, granules, tablets, capsules, injections, etc. The proper dosage depends on such factors as the disease to be managed, condition, subject and route of administration. When the compound (I) or salt thereof is used for the treatment of essential hypertension (hyperpiesia) in adult humans, it is preferably administered at the daily dose of 10 to 100 mg by the oral route or at the daily dose of 5 to 50 mg by the intravenous route in 2 to 3 divided doses.

The starting compound (II) for the present invention can be easily produced by the following combination of known reactions. The reaction steps involved will also be briefly explained.

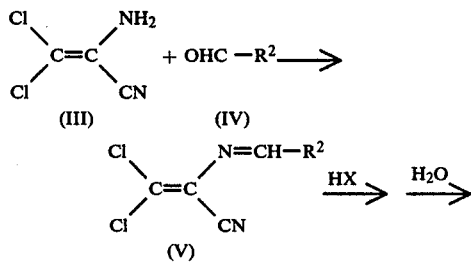

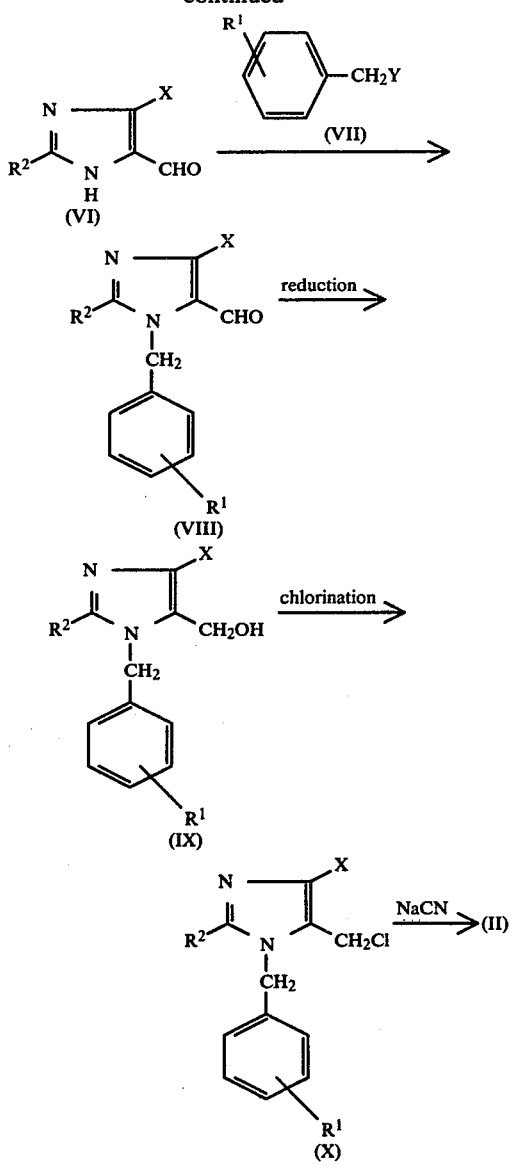

In the above formulas, $R^1$, $R^2$ and X have the meanings respectively defined hereinbefore; and Y is halogen.

By a procedure analogous to that described in "Chemical and Pharmaceutical Bulletin" 24, 960(1976), 2-amino-3,3-dichloroacrylonitrile (III) is reacted with an aldehyde of the formula (IV) to obtain a 5-formylimidazole derivative of the formula (VI) via a Schiff base of the formula (V). The reaction between compound (VI) and a benzyl halide of the formula (VII) is generally carried out in a solvent and in the presence of an acid acceptor. The acid acceptor is preferably an alkali metal carbonate such as potassium carbonate or sodium carbonate. The solvent is preferably dimethylformamide, dimethylsulfoxide or the like. Normally this reaction is conducted by heating at about 100° to 150° C. for 1 to 2 hours. While this reaction yields 1-benzyl-5-formylimidazole of the formula (VIII), as a principal product, there is normally by-produced an isomer of the formula (VIII').

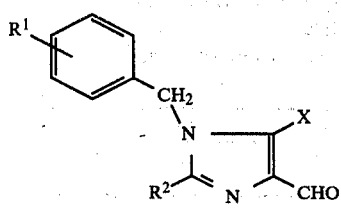

(VIII')

The separation of compound (VIII) from compound (VIII') is effected by a conventional physico-chemical process, e.g. recrystallization or chromatography. Reduction of compound (VIII) gives rise to 1-benzyl-5-hydroxymethylimidazole of the formula (IX). A preferred reduction procedure comprises reacting compound (VIII) with 0.5 to 1 molar equivalent of sodium borohydride in an alcohol-type solvent at room temperature for 1 to 2 hours. Chlorination of compound (IX) yields 1-benzyl-5-chloromethylimidazole of the formula (X). A preferred chlorination procedure consists in reacting compound (IX) with thionyl chloride in an inert solvent such as chloroform or benzene at room temperature for 1 to 2 hours. Generally, compound (X) need not be purified but, after the solvent and excess thionyl chloride are distilled off, it may be reacted with sodium cyanide to obtain the desired starting material compound of the formula (II). This reaction is effected by stirring the reactants vigorously in dimethylsulfoxide at room temperature to 50° C. for 2 to 3 hours. The isolation of compound (II) can be accomplished by the ordinary physicochemical procedure, e.g. the steps of removing the inorganic matter and subjecting the residue to recrystallization or chromatography.

The following Examples, Reference Examples and Experimental Data are intended merely to illustrate presently preferred embodiments of the present invention and not to restrict the scope of this invention.

Throughout the foregoing description as well as in the following Examples, Reference Examples and Claims, "mg", "g", "mL", "l", "°C." and "N" respectively refer to "milligram(s)", "gram(s)", "milliliter(s)", "liter(s)", "degrees centigrade" and "Normal(s)".

EXAMPLE 1

In 120 ml of 60% sulfuric acid, 20 g of 1-benzyl-2-phenyl-4-chloro-5-cyanomethylimidazole was stirred at 145° C. overnight. Under ice-cooling, the reaction mixture was neutralized with an aqueous solution of sodium hydroxide. The resulting precipitate was then recrystallized from acetonitrile, whereupon 18.9 g of 1-benzyl-2-phenyl-4-chloroimidazole-5-acetic acid was obtained as colorless needles, m.p. 161°–163° C.

Elemental analysis, for $C_{18}H_{15}N_2O_2Cl$

|        | C(%)  | H(%) | N(%) |
|--------|-------|------|------|
| Calcd. | 66.16 | 4.63 | 8.57 |
| Found  | 66.03 | 4.80 | 8.63 |

EXAMPLE 2

2.8 g of 1-benzyl-2-(p-methoxyphenyl)-4-chloro-5-cyanomethylimidazole was refluxed in a mixture of 15 ml concentrated hydrochloric acid, 15 ml water and 15 ml glacial acetic acid for 5 hours. The reaction mixture was diluted with 1 l of water and allowed to stand, whereupon 2.5 g of 1-benzyl-2-(p-methoxyphenyl)-4-chloroimidazole-5-acetic acid was obtained as colorless prisms, m.p. 192°–194° C.

Elemental analysis, for $C_{19}H_{17}N_2O_3Cl \cdot \frac{1}{2}H_2O$

|        | C(%)  | H(%) | N(%) | Cl(%) |
|--------|-------|------|------|-------|
| Calcd. | 62.40 | 4.97 | 7.66 | 9.71  |
| Found  | 62.01 | 4.88 | 7.67 | 9.33  |

EXAMPLE 3

5 g of 1-benzyl-2-(p-dimethylaminophenyl)-4-chloro-5-cyanomethylimidazole was refluxed in a mixture of 25 ml concentrated hydrochloric acid, 25 ml water and 25 ml glacial acetic acid for 3 hours. The reaction mixture was concentrated to dryness under reduced pressure, the residue dissolved in 50 ml of water and the solution adjusted to pH 3 with sodium hydrogen carbonate. The resulting precipitate was recovered by filtration and recrystallized from aqueous ethanol. By the above procedure was obtained 4 g of 1-benzyl-2-(p-dimethylaminophenyl)-4-chloroimidazole-5-acetic acid as pale yellow needles, m.p. 170°–180° C.

Elemental analysis, for $C_{20}H_{20}N_3O_2Cl$

|        | C(%)  | H(%) | N(%)  | Cl(%) |
|--------|-------|------|-------|-------|
| Calcd. | 64.95 | 5.45 | 11.34 | 9.58  |
| Found  | 64.83 | 5.53 | 11.26 | 9.22  |

EXAMPLES 4 to 12

The following compounds were synthesized by procedures similar to Examples 1 to 3.

Table 1

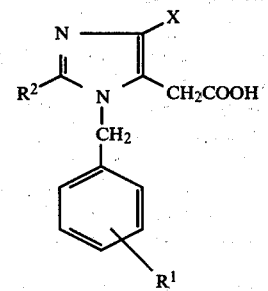

| Ex. No. | $R^1$ | $R^2$ | X | m.p. (°C.) | Recryst. solvent |
|---------|-------|-------|---|------------|------------------|
| 4 | H |  | Br | 182–183 (decomp.) | Acetonitrile |
| 5 | H | 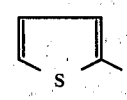 | Cl | 162–165 (decomp.) | — |
| 6 | H | 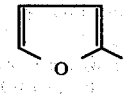 | Cl | 158–163 | Ethanol-hexane |
| 7 | H | 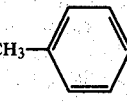 | Cl | 190–193 | Acetonitrile |

Table 1-continued

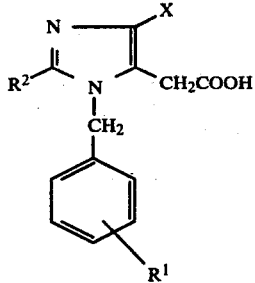

| Ex. No. | R¹ | R² | X | m.p. (°C.) | Recryst. solvent |
|---|---|---|---|---|---|
| 8 | H | i-C₃H₇—⟨phenyl⟩— | Cl | 200–205 | — |
| 9 | H | CH₃O—⟨phenyl⟩— | Cl | 175–177 | — |
| 10 | H | n-C₄H₉O—⟨phenyl⟩— | Cl | 195–196 | — |
| 11 | H | Cl—⟨phenyl⟩— | Cl | 187–189 | Aqueous ethanol |
| 12 | p-NO₂ | ⟨phenyl⟩— | Cl | 231–233 | Ethanol-hexane |

EXAMPLE 13

In 100 ml of ethanol was dissolved 2 g of 1-(p-nitrobenzyl)-2-phenyl-4-chloroimidazole-5-acetic acid, and following addition of 300 mg of 10% palladium-on-carbon, the solution was shaken in hydrogen streams for 2 hours. The catalyst was filtered off and the filtrate was concentrated to dryness under reduced pressure and recrystallized from ethanol-hexane. By the above procedure was obtained 1.4 g of 1-(p-aminobenzyl)-2-phenyl-4-chloroimidazole-5-acetic acid as colorless needles, m.p. 141°–145° C. (decomp.)

Elemental analysis, for $C_{18}H_{16}N_3O_2Cl$

|  | C(%) | H(%) | N(%) | Cl(%) |
|---|---|---|---|---|
| Calcd. | 63.25 | 4.72 | 12.29 | 10.37 |
| Found | 62.66 | 4.70 | 11.91 | 9.96 |

EXAMPLE 14

In 100 ml of ethanol was dissolved 6.53 g of 1-benzyl-2-phenyl-4-chloroimidazole-5-acetic acid and under ice-cooling, hydrogen chloride was introduced until saturation. The solution was further stirred at room temperature overnight. The reaction mixture was concentrated to dryness under reduced pressure and the concentrate was run onto a column of 200 g silica gel, elution being carried out with benzene-chloroform (1:1). By the above procedure was obtained 2.28 g of 1-benzyl-2-phenyl-4-chloro-5-ethoxycarbonylmethylimidazole as crude crystals, which were then recrystallized from diethyl ether-hexane. Colorless needles, m.p. 72°–73° C.

Elemental analysis, for $C_{20}H_{19}N_2O_2Cl$

|  | C(%) | H(%) | N(%) |
|---|---|---|---|
| Calcd. | 67.70 | 5.40 | 7.89 |
| Found | 67.55 | 5.23 | 7.84 |

EXAMPLE 15

3.08 g of 1-benzyl-2-phenyl-4-chloro-5-cyanomethylimidazole was dissolved in 20 ml of ethanol containing 0.3 g of hydrogen chloride and, in a sealed tubular reactor, the solution was heated at 80° C. for 10 hours. The reaction mixture was concentrated to dryness under reduced pressure and, then, treated as in Example 14. By the above procedure was obtained 0.9 g of 1-benzyl-2-phenyl-4-chloro-5-ethoxycarbonylmethylimidazole, m.p. 72°–73° C.

In 20 ml of ethanol was dissolved 1 g of the above product, and following addition of 5 ml of a 2N-aqueous solution of sodium hydroxide, the solution was boiled for 5 hours. To this reaction mixture was added 5 ml of 2N-hydrochloric acid and the ethanol was distilled off under reduced pressure. By the above procedure was obtained 0.5 g of 1-benzyl-2-phenyl-4-chloroimidazole-5-acetic acid as colorless needles, m.p. 161°–163° C.

EXAMPLE 16

In 20 ml of ethanol was dissolved 3.27 g of 1-benzyl-2-phenyl-4-chloroimidazole-5-acetic acid and, then, a solution of 0.4 g of sodium hydroxide in 2 ml of water was added. To this mixture was added 20 ml of acetone, followed by addition of 20 ml of diethyl ether. The mixture was then allowed to stand, whereupon 3.5 g of the sodium salt of 1-benzyl-2-phenyl-4-chloroimidazole-5-acetic acid was obtained as white crystalline powders, m.p. 288°–292° C.

EXAMPLE 17

As a hypotensive drug, for instance, the compound (I) of this invention can be employed in the following formulations.

| 1. Tablets | | |
|---|---|---|
| (1) | 1-Benzyl-2-(p-dimethylaminophenyl)-4-chloroimidazole-5-acetic acid | 10 mg |
| (2) | Lactose | 35 mg |
| (3) | Corn starch | 150 mg |
| (4) | Microcrystalline cellulose | 30 mg |
| (5) | Magnesium stearate | 5 mg |
| | | 230 mg/tablet |

The whole amounts of (1), (2) and (3), two-thirds of the indicated amount of (4) and one-half of the indicated amount of (5) are admixed together and the mixture is granulated. The remaining amounts of (4) and (5) are added to the granules, followed by compression-molding into tablets.

| 2. Capsules | | |
|---|---|---|
| (1) | 1-Benzyl-2-phenyl-4-chloroimidazole-5-acetic acid | 20 mg |
| (2) | Lactose | 90 mg |

-continued

| 2. Capsules | | |
|---|---|---|
| (3) | Microcrystalline cellulose | 70 mg |
| (4) | Magnesium stearate | 10 mg |
| | | 190 mg/capsule |

The whole amounts of (1), (2) and (3) are admixed with one-half of the indicated amount of (4) and the mixture is granulated. The remaining half of (4) is added to the granules and the entire mixture is sealed into a gelatin capsule.

| 3. Injections | | |
|---|---|---|
| (1) | Sodium salt of 1-benzyl-2-phenyl-4-chloro-imidazole-5-acetic acid | 10 mg |
| (2) | Inositol | 100 mg |
| (3) | Benzyl alcohol | 20 mg |

The whole amounts of (1), (2) and (3) are dissolved in a sufficient amount of distilled water for injection to make a total of 2 ml and the solution is sealed into an ampoule. This process is entirely carried out under sterile conditions.

REFERENCE EXAMPLE 1

In a reaction vessel fitted with a water-separating funnel, 15 g of 2-amino-3,3-dichloroacrylonitrile and 17.8 g of p-butoxybenzaldehyde were refluxed together in 200 ml of toluene for 9 hours, with the byproduct water being expelled. The reaction mixture was concentrated to dryness under reduced pressure, and following addition of 100 ml of methanol, the residue was allowed to cool, whereupon 25 g of 2-(p-butoxybenzyliden-)amino-3,3-dichloroacrylonitrile was obtained as yellow needles, m.p. 74° C. This product was dissolved in 500 ml of diethyl ether and, after the solution was saturated with hydrogen chloride under ice-cooling, was allowed to stand at room temperature for 3 days. The resulting crystals were recovered by filtration and heated with 300 ml of water at 90°–100° C. for one hour. After cooling, the precipitate was recovered by filtration and recrystallized from aqueous ethanol. By the above procedure was obtained 20 g of 2-(p-butoxyphenyl)-4-chloro-5-formylimidazole as light-brown needles, m.p. 185°–187° C.

REFERENCE EXAMPLE 2

In a reaction vessel fitted with a water-separating funnel, 40 g of 2-amino-3,3-dichloroacrylonitrile and 40 g of p-dimethylaminobenzaldehyde were heated on reflux in 400 ml of toluene for 13 hours. The reaction mixture was concentrated to about 50 ml and, then, allowed to cool. By the above procedure was obtained 60 g of 2-(p-dimethylaminobenzyliden)amino-3,3-dichloroacrylonitrile as yellow needles, m.p. 134°–135° C. This product was dissolved in 800 ml of dioxane and after the solution was saturated with hydrogen chloride at room temperature, it was stirred at 50°–60° C. for 2 days. After cooling, the resulting precipitate was recovered by filtration and suspended in 600 ml of water. This suspension was stirred at 90° C. for an hour, while sodium hydrogen carbonate was added to neutralize the system. On cooling, there was obtained a blackish-brown precipitate of 2-(p-dimethylaminophenyl)-4-chloro-5-formylimidazole, which was recovered by filtration. Yield 27 g.

REFERENCE EXAMPLE 3

The following compounds were obtained by procedures similar to Reference Examples 1 and 2.

Table 2

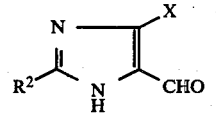

| $R^2$ | X | m.p. (°C.) | Rcryst. solvent |
|---|---|---|---|
| 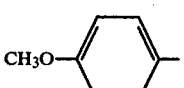 | Cl | 225–227 | Methanol |
| 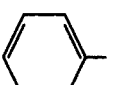 | Br | 191–192 | Dioxane |
| 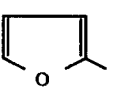 | Cl | — | — |
| 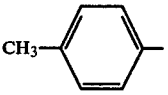 | Cl | 223–224 | Methanol |
| 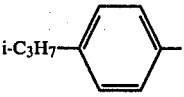 | Cl | 185–187 | Aqueous ethanol |
| 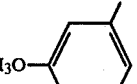 | Cl | 163–164 | Aqueous methanol |
| 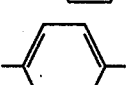 | Cl | — | — |
| 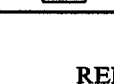 | Cl | 275–277 | Ethanol |

REFERENCE EXAMPLE 4

In 150 ml of dimethylformamide, there were stirred 206.5 g of 2-phenyl-4-chloro-5-formylimidazole, 133 g of benzyl chloride and 103.5 g of anhydrous potassium carbonate at 110°–120° C. for an hour. The reaction mixture was poured in ice-water and the resulting precipitate was recovered by filtration and recrystallized from acetonitrile twice. By the above procedure was obtained 143 g of 1-benzyl-2-phenyl-4-chloro-5-formylimidazole as colorless needles, m.p. 117°–118° C.

REFERENCE EXAMPLE 5

In 50 ml of dimethylformamide, there were stirred 10.3 g of 2-phenyl-4-chloro-5-formylimidazole, 11.3 g of p-nitrobenzyl bromide and 5.2 g of anhydrous potassium carbonate at 110°–120° C. for 2 hours. The reaction mixture was poured in ice-water and the resulting precipitate was put on a column of 100 g silica gel, elution being carried out with chloroform. The first fraction was concentrated to dryness and recrystallized from ethanol. By the above procedure was obtained 13.6 g of 1-(p-nitrobenzyl)-2-phenyl-4-chloro-5-formylimidazole as colorless needles, m.p. 150°–152° C.

REFERENCE EXAMPLE 6

The following compounds were obtained by procedures similar to Reference Examples 5 and 6.

Table 3

(VIII)

Structure: R²-C(=N-)-N(CH₂-phenyl)-C(CHO)=C(X)- (imidazole with X at 4-position, CHO at 5-position, N-benzyl, R² at 2-position)

| R² | X | m.p.(°C.) | Recryst. solvent |
|---|---|---|---|
| CH₃O—C₆H₄— (p) | Cl | 83–85 | Methanol |
| (CH₃)₂N—C₆H₄— (p) | Cl | 151–153 | Dioxane-methanol |
| C₆H₅— | Br | 96–97 | Ethanol |
| 2-thienyl | Cl | 151–152 | Ethanol |
| 2-furyl | Cl | — | — |
| CH₃—C₆H₄— (p) | Cl | 116–117 | Methanol |
| i-C₃H₇—C₆H₄— (p) | Cl | 66–67 | Methanol |
| CH₃O—C₆H₄— (m) | Cl | 84–86 | Methanol |
| n-C₄H₉O—C₆H₄— (p) | Cl | 80–81 | Methanol |
| Cl—C₆H₄— (p) | Cl | 130–131 | Methanol |

REFERENCE EXAMPLE 7

In 300 ml of methanol was dissolved 29.65 g of 1-benzyl-2-phenyl-4-chloro-5-formylimidazole, and under stirring at room temperature, 1.23 g of sodium borohydride was added in portions, whereby a reaction took place with the evolution of heat. After one hour the solvent was distilled off and cold water was added to the residue. The insolubles, i.e. colorless crystals of 1-benzyl-2-phenyl-4-chloro-5-hydroxymethylimidazole, were collected by filtration. 30.36 g; m.p. 175°–177° C.

REFERENCE EXAMPLE 8

In 45 ml of methanol was dissolved 4 g of 1-benzyl-2-(p-methoxyphenyl)-4-chloro-5-formylimidazole, and following addition of 0.18 g of sodium borohydride, the solution was stirred at room temperature for 2 hours. To this reaction mixture was added 10 ml of water, followed by addition of 0.3 ml of glacial acetic acid. The mixture was then allowed to cool, whereupon 3 g of 1-benzyl-2-(p-methoxyphenyl)-4-chloro-5-hydroxymethylimidazole was obtained as colorless needles, m.p. 148°–149° C.

REFERENCE EXAMPLE 9

The following compounds were obtained by procedures similar to Reference Examples 7 and 8.

(IX)

Structure: R²-C(=N-)-N(CH₂-C₆H₄-R¹)-C(CH₂OH)=C(X)- (imidazole with X at 4-position, CH₂OH at 5-position, N-benzyl substituted with R¹, R² at 2-position)

| R¹ | R² | X | m.p.(°C.) | Recryst. solvent |
|---|---|---|---|---|
| H | (CH₃)₂N—C₆H₄— (p) | Cl | 195–196 | Methanol |
| H | C₆H₅— | Br | 180–181 | Methanol |
| H | 2-thienyl | Cl | — | — |
| H | 2-furyl | Cl | — | — |
| H | CH₃—C₆H₄— (p) | Cl | 169–171 | Methanol |
| H | i-C₃H₇—C₆H₄— (p) | Cl | 175–176 | Methanol |
| H | CH₃O—C₆H₄— (m) | Cl | 144–145 | — |
| H | n-C₄H₉O—C₆H₄— (p) | Cl | 115–117 | — |

Ethyl

-continued

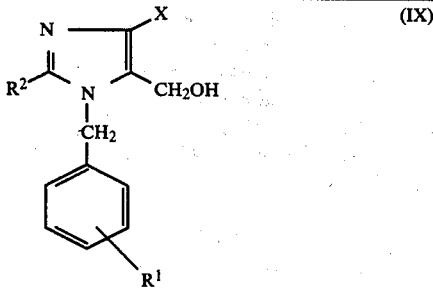

| R¹ | R² | X | m.p.(°C.) | Recryst. solvent |
|---|---|---|---|---|
| P—NO₂ | phenyl | Cl | 186 | acetate |
| H | 4-Cl-phenyl | Cl | 191–192 | — |

REFERENCE EXAMPLE 10

In 150 ml of chloroform was suspended 29.88 g of 1-benzyl-2-phenyl-4-chloro-5-hydroxymethylimidazole, and under stirring at room temperature, 23.8 g of thionyl chloride was added dropwise, whereupon a reaction took place with the evolution of heat. The reaction mixture was concentrated to dryness under reduced pressure and the residue washed with benzene to recover 35.4 g pale yellow powders of 1-benzyl-2-phenyl-4-chloro-5-chloromethylimidazole. 25.2 g of finely powdered sodium cyanide was added in small portions to 85 ml of dimethylsulfoxide to prepare a suspension and while this suspension was stirred, 85 ml of a dimethylsulfoxide solution of the above chloromethyl compound was added dropwise. After the dropwise addition had been completed, the mixture was stirred at room temperature for 2 hours and, then, poured in ice-water. It was then extracted with 500 ml of ethyl acetate and the extract was washed with water and dried. The solvent was distilled off from this solution, the residue was run onto a column of 200 g silica gel, and elution was carried out with benzene-ethyl acetate (19:1). By the above procedure was obtained 21.2 g of 1-benzyl-2-phenyl-4-chloro-5-cyanomethylimidazole as yellow powders. A portion of this product was recrystallized from diethyl ether. m.p. 121°–122° C.

REFERENCE EXAMPLE 11

In 31 ml of chloroform was suspended 7.5 g of 1-benzyl-2-(p-dimethylaminophenyl)-4-chloro-5-hydroxymethylimidazole, and 3.1 ml of thionyl chloride was added dropwise. The mixture was stirred at room temperature for 2 hours, at the end of which time it was concentrated to dryness under reduced pressure. To the residue was added 30 ml of toluene and the mixture concentrated to dryness under reduced pressure. This product was dissolved in 25 ml of dimethylsulfoxide, and at 40°–50° C., this solution was added, dropwise and with stirring, to a suspension of 6.2 g sodium cyanide in dimethylsulfoxide. The mixture was stirred at that temperature for 2 hours, after which time 300 ml of chloroform was added, followed by washing twice with 400 ml portions of water. The chloroform layer was concentrated to dryness under reduced pressure, the residue run onto a column of 80 g silica gel, and elution carried out with chloroform. The main fraction was concentrated to dryness under reduced pressure, whereupon 5 g of 1-benzyl-2-(p-dimethylaminophenyl)-4-chloro-5-cyanomethylimidazole as pale yellow crystals. A portion of this product was recrystallized from methanol to obtain pale yellow needles melting at 147°–149° C.

REFERENCE EXAMPLE 12

The following compounds were obtained by procedures analogous to Reference Examples 10 and 11.

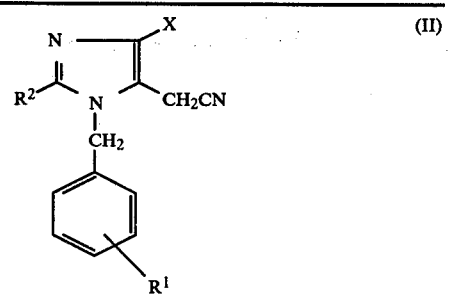

| R¹ | R² | X | m.p.(°C.) | Recryst. solvent |
|---|---|---|---|---|
| H | 4-CH₃O-phenyl | Cl | 97–97 | Methanol |
| H | phenyl | Br | 111–112 | Diethyl ether |
| H | 2-thienyl (methyl) | Cl | 121–122 | Diethyl ether |
| H | 2-furyl (methyl) | Cl | 118 | Methanol |
| H | 4-CH₃-phenyl | Cl | 130–131 | Ethanol |
| H | 4-i-C₃H₇-phenyl | Cl | Oil | — |
| H | 4-CH₃O-phenyl | Cl | 116–118 | Methanol |
| H | 4-n-C₄H₉O-phenyl | Cl | Oil | — |
| H | 4-Cl-phenyl | Cl | 127–128 | Methanol |

Chloroform-

-continued

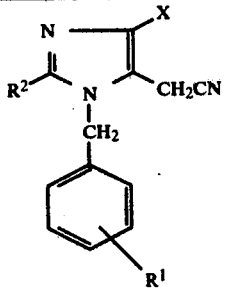

| $R^1$ | $R^2$ | X | m.p.(°C.) | Recryst. solvent |
|---|---|---|---|---|
| p-NO$_2$ |  | Cl | 188-189 | hexane |

EXPERIMENTAL DATA

The diuretic actions of some representative species of the compound (I) of this invention are summarized in Table 6. The test was performed in rats by the procedure of W. L. Lipschitz [J. Pharmacol. Exp. Ther. 79, 97 (1943).] Table 6 shows the values for dosed groups, with the values for the control groups being assumed to be 1.00. Thus, $$UV = \frac{\text{Urine volume of rats in dosed group (ml/5 hrs./100g. body weight)}}{\text{Urine volume of rats in control group (ml/5 hrs./100 g body weight)}}$$

$$U_{Na}V = \frac{\text{Amount of Na secreted by rats in dosed group } (\mu \text{ equiv./5 hrs./100 g body weight)}}{\text{Amount of Na secreted by rats in control group } (\mu \text{ equiv./5 hrs./100 g body weight)}}$$

$$U_KV = \frac{\text{Amount of K secreted by rats in dosed group } (\mu \text{ equiv./5 hrs./100 g body weight)}}{\text{Amount of K secreted by rats in control group } (\mu \text{ equiv./5 hrs./100 g body weight)}}$$

Table 6

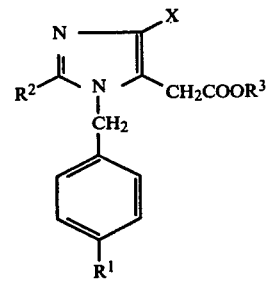

| Compound | | | | Dosage (mg/kg, oral) | Diuretic action | | |
|---|---|---|---|---|---|---|---|
| $R^1$ | $R^2$ | $R^3$ | X | | V | $U_{Na}V$ | $U_KV$ |
| H | phenyl | H | Cl | 30 | 1.86* | 1.77* | 1.15 |
| | | | | 100 | 3.34*** | 3.03*** | 1.98* |
| H | phenyl | H | Br | 100 | 2.99*** | 2.58** | 1.60** |
| H | 4-CH$_3$-phenyl | H | Cl | 100 | 2.84*** | 2.46*** | 2.01** |
| H | 2-thienyl | H | Cl | 100 | 2.36** | 1.97** | 1.68* |
| H | phenyl | C$_2$H$_5$ | Cl | 100 | 2.48*** | 1.88** | 1.89** |
| H | 4-(CH$_3$)$_2$N-phenyl | H | Cl | 10 | 3.18*** | 2.83*** | 1.90** |
| | | | | 30 | 4.47*** | 3.98*** | 2.48*** |
| | | | | 100 | 5.28*** | 4.69*** | 2.77*** |
| H | 3-CH$_3$O-phenyl | H | Cl | 30 | 1.69*** | 1.62** | 1.65** |

Table 6-continued

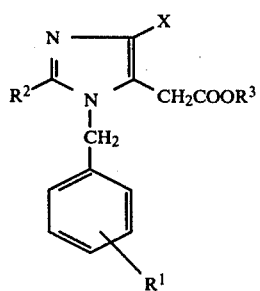

| Compound | | | | Dosage (mg/kg, | Diuretic action | | |
| --- | --- | --- | --- | --- | --- | --- | --- |
| $R^1$ | $R^2$ | $R^3$ | X | oral) | V | $U_{Na}V$ | $U_KV$ |
| H | n-$C_4H_9O$—⌬— | H | Cl | 30 | 1.57* | 1.58* | 1.29 |
| $NH_2$ | ⌬— | H | Cl | 30 | 1.97*** | 1.72*** | 1.49* |
| H | i-$C_3H_7$—⌬— | H | Cl | 30 | 1.82** | 1.58* | 1.42 |

\*: P<0.05,
\*\*: P<0.01,
\*\*\*: P<0.001

What is claimed is:

1. A compound of the formula:

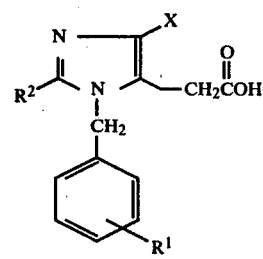

wherein
$R^1$ is hydrogen, nitro or amino;
$R^2$ is a phenyl, furyl or thienyl group unsubstituted or substituted by halogen, lower alkyl, lower alkoxy or di-lower-alkylamino;
$R^3$ is hydrogen or lower alkyl; and
X is halogen;
or a pharmaceutically acceptable salt thereof.

2. A compound according to claim 1, wherein the salt is a physiologically acceptable salt.

3. A compound according to claim 1, wherein X is chlorine.

4. A compound according to claim 1, which is 1-benzyl-2-(p-dimethylaminophenyl)-4-chloroimidazole-5-acetic acid.

5. A compound according to claim 1, which is 1-benzyl-2-phenyl-4-chloroimidazole-5-acetic acid.

6. A compound of the formula:

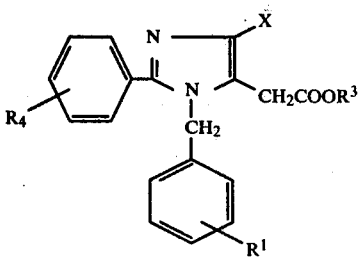

wherein
$R^1$ is hydrogen, nitro or amino;
$R^2$ is a phenyl, furyl or thienyl group unsubstituted or substituted by halogen, lower alkyl, lower alkoxy or di-lower-alkylamino; and
X is halogen
or a pharmaceutically acceptable salt thereof.

7. A compound of the formula:

wherein
$R^1$ is hydrogen, nitro or amino;
$R^3$ is hydrogen or lower alkyl;
$R_4$ is a hydrogen, halogen, lower alkyl, lower alkoxy or di-lower-alkylamino; and X is halogen
or a pharmaceutically acceptable salt thereof.

8. A compound of claim 7, wherein R₄ is hydrogen.

9. A compound of claim 7, wherein R₄ is para-di-lower alkyl-amino.

10. A compound of the formula:

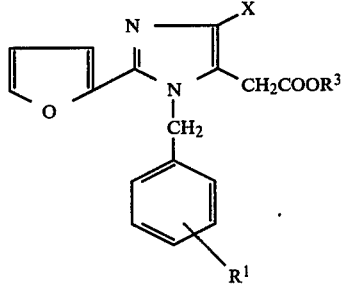

wherein
$R^1$ is hydrogen, nitro or amino;
$R^3$ is hydrogen or lower alkyl; and
X is halogen
or a pharmaceutically acceptable salt thereof.

11. A compound of the formula:

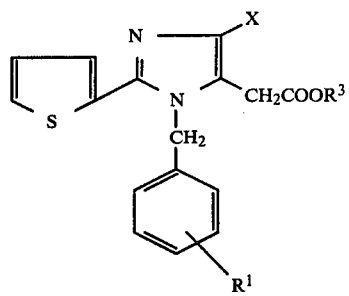

wherein
$R^1$ is hydrogen, nitro or amino;
$R^3$ is hydrogen or lower alkyl; and
X is halogen
or a pharmaceutically acceptable salt thereof.

12. A method of treating a patient suffering from hypertension to alleviate said hypertension which comprises administering to said patient a compound of claim 1, 3, 4, 5, 6, 7, 10 or 11 in an amount sufficient to alleviate said hypertension.

13. A method of treating a patient to alleviate edema which comprises administering to said patient a compound of claim 1, 3, 4, 5, 6, 7, 10 or 11 in an amount sufficient to alleviate said edema.

* * * * *